(12) United States Patent
Yamanaka et al.

(10) Patent No.: US 7,012,136 B2
(45) Date of Patent: Mar. 14, 2006

(54) STIMULUS RESPONSIVE AFFINITY CHROMATOGRAPHIC MATERIAL AND SEPARATION/PURIFICATION METHOD

(75) Inventors: Hidenori Yamanaka, Sodegaura (JP); Yukio Hasegawa, Ichikawa (JP)

(73) Assignees: Amersham Biosciences KK, Tokyo (JP); Teruo Okano, Chiba (JP)

( * ) Notice: Subject to any disclaimer, the term of this patent is extended or adjusted under 35 U.S.C. 154(b) by 50 days.

(21) Appl. No.: 10/381,120

(22) PCT Filed: Oct. 15, 2001

(86) PCT No.: PCT/JP01/09035

§ 371 (c)(1), (2), (4) Date: Jul. 7, 2003

(87) PCT Pub. No.: WO02/30564

PCT Pub. Date: Apr. 18, 2002

(65) Prior Publication Data

US 2004/0039177 A1 Feb. 26, 2004

(30) Foreign Application Priority Data

Oct. 13, 2000 (JP) ............................. 2000-313952

(51) Int. Cl.
*A23J 1/00* (2006.01)

(52) U.S. Cl. .................. 530/412; 530/413; 530/395

(58) Field of Classification Search ............. 530/350, 530/391.1, 387, 395, 412, 413; 424/78.08, 424/178.1, 193.1, 280; 525/54.1; 435/69.1

See application file for complete search history.

(56) References Cited

U.S. PATENT DOCUMENTS 6,084,062 A   7/2000  Maclennan et al.

FOREIGN PATENT DOCUMENTS

| EP | 534016 | 3/1993 |
|---|---|---|
| JP | 7-136505 | 5/1995 |
| JP | 8-103653 | 4/1996 |
| JP | 9-49830 | 2/1997 |
| JP | 11-171928 | 6/1999 |
| JP | 2000-140632 | 5/2000 |
| WO | WO00/67901 | 11/2000 |

OTHER PUBLICATIONS

Kanazawa et al., Temprature-responsive chromatography, 1998, Trends in Analytical Chemistry, vol. 17, No. 7 pp. 435-440.*

Yamanaka et al., Development of Temprature Regulated Elution System for Lectin Affinity Chromatography, 2000, Chromatography, vol. 21, No. 4 pp. 324-325.*

* cited by examiner

*Primary Examiner*—Jon Weber
*Assistant Examiner*—Robert B. Mondesi
(74) *Attorney, Agent, or Firm*—Royal N. Ronning, Jr.; Yonggang Ji

(57) ABSTRACT

A separation material characterized by supporting, in its surface, a linear or crosslinked stimulus responsive polymer to which a substance A having specific affinity for a target substance and a low-molecular substance B having specific affinity for the substance A have been bonded. Such a separation material can increase the recovery of a target substance to be purified and do not require desalting and hapten sugar-eliminating operations and, in addition, have high productivity.

15 Claims, 3 Drawing Sheets

STIMULUS RESPONSIVE AFFINITY CHROMATOGRAPHIC MATERIAL AND SEPARATION/PURIFICATION METHOD

This application is a 371 of PCT/JP01/09035 filed Oct. 15, 2001.

TECHNICAL FIELD

The present invention relates to a separation material supporting, in its surface, a substance having specific affinity for a target substance and a low-molecular substance having specific affinity for that substance either directly or through a stimulus responsive polymer, and to a substance separation method employing the separating material.

BACKGROUND ART

Separation and purification of biocomponents and drugs are commonly performed by ion-exchange chromatography, reverse phase chromatography, affinity chromatography and the like. Of them, the affinity chromatography is the only method for effective purification of almost all biomolecules based on their biological functions or individual chemical structures and is a very unique separation technique.

Affinity chromatography is one type of adsorption chromatography in which the substance to be purified is specifically and reversibly adsorbed onto a bound substance (ligand) which has been immobilized on an insoluble carrier (matrix). It is widely applied to the separation and purification of biological substances since most separations can be accomplished in one stage and a remarkable time saving can be achieved compared to a multi-stage method with low in selectivity.

However, according to the common affinity chromatography, the salt concentration, the organic solvent concentration, the pH and the like of an eluent are varied in the elution of the biocomponents, drugs, recombinant proteins and the like which come to target substances or a gradient of a substance to be competitively bonded to the ligand is used. It is known that such methods are sometimes reduced in recovery since the conditions such as the salt concentration and the organic solvent concentration often become severe with respect to the target substance. Furthermore, the salt, the organic solvent and the substance to be competitively bonded to the ligand which have been used in the elution of the target substance must finally be removed by operations such as desalting and drying but, when the substance to be competitively bonded to the ligand and the target substance are of a similar molecular size, it is very difficult or sometimes impossible to separate the target substance from the substance used in the elution. In addition, the activity and the recovery of the final substance are often significantly reduced by the operations of desalting and drying.

In eluting a target substance, the elution by changing the composition of an eluent such as the salt, the organic solvent, the pH, the concentration of the substance to be competitively bonded to a ligand can cause the above described problems such inactivation, reduction in recovery and the like by the use of chemical substances including, for example, salts, organic solvents, acids and bases in the eluent and substances to be competitively bonded to ligands. However, if it is possible to create an environment which affects the elution of a target substance not by such chemical methods but by physical changes such as heat, light and magnetism, it would be possible to elute the target substance by a physical means to solve the problems of inactivation and reduction in recovery and the like.

Recently, the description relating to separation materials comprising stimulus responsive polymers covalently bonded to ion-exchange groups has been found (see, for example, Japanese Patent Application No. Hei 10-140722 and its counterpart WO 99-61904).

Galaev et al., Journal of Chromatography A684 (1994) 37–43 describe the elution by temperature of lactate dehydrogenase (LDH) in a chromatographic system using a base matrix to which Cibacron Blue is covalently bonded and on which a temperature responsive polymer (polyvinyl caprolactam) is also physically adsorbed. However, the clouding point of the polyvinyl lactam is 38° C. and it is necessary to raise temperature up to 40° C. in adsorbing the polyvinyl lactam on the base matrix and thus, there is a fear of causing denaturation depending on the target protein used. In general, the clouding point can be lowered by introducing a hydrophobic group but in this instance, it can be anticipated that the recovery will be decreased by an increase of non-specific adsorption on the hydrophobic group.

Hofman et al., (WO 87/06152) describe a separation method using a ligand bonded to a temperature responsive polymer. Furthermore, in WO97/09068 there is proposed a separation method by molecular conjugates obtained by introducing a stimulus responsive polymer into a substance having specific affinity for a target substance.

Further, in Japanese Patent Publication (Kokai) No. Hei. 7-135957/1995 and WO 97/09068 there are described separation materials constituted by a substance having specific affinity for a target substance and a stimulus responsive polymer.

However, none of these patents suggest a technique for increasing the efficiency of the elution by temperature by immobilizing a substance having affinity for a target substance and a low molecular substance which competitively binds to a ligand.

There are also a number of publications which describe chromatography based on separation materials comprising stimulus responsive polymers which do not have a ligand covalently bonded to temperature responsive polymers. Gewehr et al. [Macromolecular Chemistry and Physics 193 (1992) 249–256] describe gel chromatography on porous silica beads coated with a stimulus responsive polymer. Hosoya et al. [Anal. Chem. 67 (1995) 1907–1911]; Yamamoto et al. [Proc. 114th National Meeting of the Pharmaceutical Society of Japan, Tokyo (1994) 160]; Kanazawa et al. [Yakugaku Zasshi 117 (10–11) (1997) 817–824]; Kanazawa et al. [Anal. Chem. 68(1) (1996) 100–105]; Kanazawa et al. [Anal. Chem. 69(5) (1997) 823–830]; Kanazawa et al. [J. Pharm. Biomed. Anal. 15 (1997) 1545–1550]; Yakushiji et al. [Langmuir 14(16) 1998) 4657–466268]; Kanazawa et al. [Trends Anal. Biochem. 17(7) (1998) 435–440]; Yakushiji et al. [Anal. Chem. 71(6) 1999] 1125–1130); Grace & Co. (EP 534016); and Okano [Japanese Patent Publication (Kokai) No. Hei 6-108643/1994] all describe reversed phase chromatography on a matrix coated with a heat responsive polymer for aiming to separate biopolymers. The matrix can be porous. The utilized hydrophobic groups are possessed by the polymer as such. In these-prior art documents there is no description of ligands covalently bonded to the polymer after polymerization.

Furthermore, the following various separation materials using stimulus responsive polymers are proposed.

In Japanese Patent Publication No. Hei 7-136505/1995 there is a description that with the use of an affinity separation material in which a substance having specific affinity for a target substance is bonded to a stimulus responsive polymer through a spacer comprising a bound substance composed of two compounds having bindability to each other (for example, avidin-biotin), the dissociation between the two compounds is caused by a stimulus (for example, temperature) to recover the target substance. However, acceleration of sufficient dissocia-tion cannot be obtained by the structural change of the polymer due to the stimulus and in the case of cells the recover is as low as about 50%.

In Japanese Patent Publication (Kokai) No. Hei 8-103653/1996 and Japanese Patent Publication (kokai) No. Hei 9-49830/1997 there is a description relating to a separation/purification method characterized in that in the stimulus responsive separation material having a region composed of a stimulus responsive polymer chain and a region having affinity for a target substance in the surface of a base matrix, after the target substance is adsorbed on the separation material, the target substance is released from the separation material by varying the structure of higher order of the stimulus responsive polymer. However, also in this instance, acceleration of sufficient dissociation by the structural change of the polymer due to a stimulus cannot be obtained and thus, the recovery is as low as 63% even in the case of cells.

In WO 94-15951 is described a method of separating a substance with the use of an affinity separation material using a composite ligand comprising a ligand bonded to a target substance having bindability weaker than the bindability of the first target substance. Also, this publication describes use of a stimulus responsive polymer but does not suggest simultaneous use of a lower-molecular substance.

However, according to the methods described in these publications, it is difficult to purify a target substance with a high recovery without changing the composition of an eluent. When the target substance to be purified, particularly by a lectin affinity chromatography, is a low-molecular compound such as a sugar chain, use of the lectin affinity chromatography is sometimes limited due to the difficulty in separating the sugar chain from a hapten sugar if the hapten sugar is used in the elution. Furthermore, there have been problems in increasing detection sensitivity and regenerating carriers.

DISCLOSURE OF INVENTION

To solve the above described problems, the present inventors have made various investigations and developments on the elution of a target substance by a physical technique. As the result, it has been found that the separation material characterized by supporting a linear or crosslinked stimulus responsive polymer bonded to both a substance A having specific affinity for a target substance and a low-molecular substance B having affinity for the substance A in the surface of a separation material can elute a target substance by adsorbing the target substance on the substance A and subsequently providing a stimulus to the stimulus responsive polymer to exceed the transition point of the stimulus responsive polymer to create a state in which a competitive reaction easily occurs between the low-molecular compound B and the target substance in their polymer chains or among the polymers by causing a structural change in the stimulus responsive polymer chain, and the present invention has been completed on the basis of such knowledge.

The present invention is to provide separation materials or separation methods which will be described in the following (1) to (9).

(1) A separation material characterized by supporting, in its surface, a linear or crosslinked stimulus responsive polymer with which both a substance A having specific affinity for a target substance and a low-molecular substance B having specific affinity for the target substance A have been bonded.

(2) A separation material characterized by supporting, in its surface, a linear or crosslinked stimulus responsive polymer to which only a substance A having specific affinity for a target substance has been bonded and a linear or crosslinked stimulus responsive polymer to which only a low-molecular substance B having specific affinity for the target substance has been bonded.

(3) A separation material characterized by directly support-ing a substance A having specific affinity for a target substance or a low-molecular substance B having specific affinity for the target substance A on a base matrix and, at the same time, supporting a linear or crosslinked stimulus responsive polymer to which the substance A or the substance B has been bonded in the surface of the separating material.

(4) A separation material of any one of the above described (1), (2) and (3), wherein the target substance is a sugar chain or a glycoprotein; the substance A having specific affinity for the target substance is a sugar affinity substance having affinity for the specific structure of a sugar chain such as a lectin; the low-molecular substance B having specific affinity for the substance A is a hapten sugar; and the stimulus responsive polymer is poly(N-isopropyl acrylamide).

(5) A separation material of any one of the above described separation materials (1) to (4) which is prepared by rendering poly(N-acryloyl succinimide) water soluble by introducing a compound having an amino group in an amount of 50 to 97 mol %, based on the succinimide group of the poly(N-acryloyl succinimide), thereinto, then introducing the substance A into the resulting water soluble polymer chain in the presence of the low-molecular substance B and subsequently immobilizing the resulting polymer on the separation material or immobilizing the resulting water soluble polymer on the separation material in the presence of both of the substance A and the low-molecular substance B.

(6) A packing for affinity chromatography comprising a separation material of any one of the above described (1), (2), (3), (4) and (5).

(7) A separation/purification method characterized by adsorbing a target substance on a separation material supporting any one of the above described stimulus responsive polymers of (1) to (4) and varying the molecular structure of the stimulus responsive polymer while changing or not changing the liquid composition of an eluent such as the salt condition and the pH to effect the competitive reaction between the target substance and the low-molecular substance B, thereby eluting the target substance.

(8) A separation/purification method characterized by adsorbing a target substance on a separation material supporting any one of the above described stimulus responsive polymers of (1) to (4) which is a temperature responsive polymer at a tempera-ture of not higher than the lower critical solution temperature (LCST) if the stimulus responsive polymer has a lower critical solution temperature (LCST) or at a temperature of not lower than the upper critical solution temperature (UCST) if the stimulus responsive polymer has an upper critical solution temperature (UCST) and varying the molecular structure of the stimulus responsive polymer by changing the column temperature to exceed the critical solution temperature of the stimulus responsive polymer while changing or not changing the liquid composition of an eluent such as the salt condition and the pH to effect the competitive reaction between the target substance and the low molecular substance B, thereby in eluting the target substance.

(9) A substance separation/purification method of the above described (7) or (8) employing chromatography.

In the invention described in WO 94/15951 the part which corresponds to the low-molecule substance B of the present invention is composed of a stimulus responsive polymer and thus, the constitution of this invention is different from that of the separation material of the present invention. Further, the invention described in WO 97/09068 introduces a stimulus responsive polymer as such into the substance A of the present invention and thus, its constitution is different from that of the present invention.

BEST MODE FOR CARRYING OUT THE INVENTION

Figure 1:
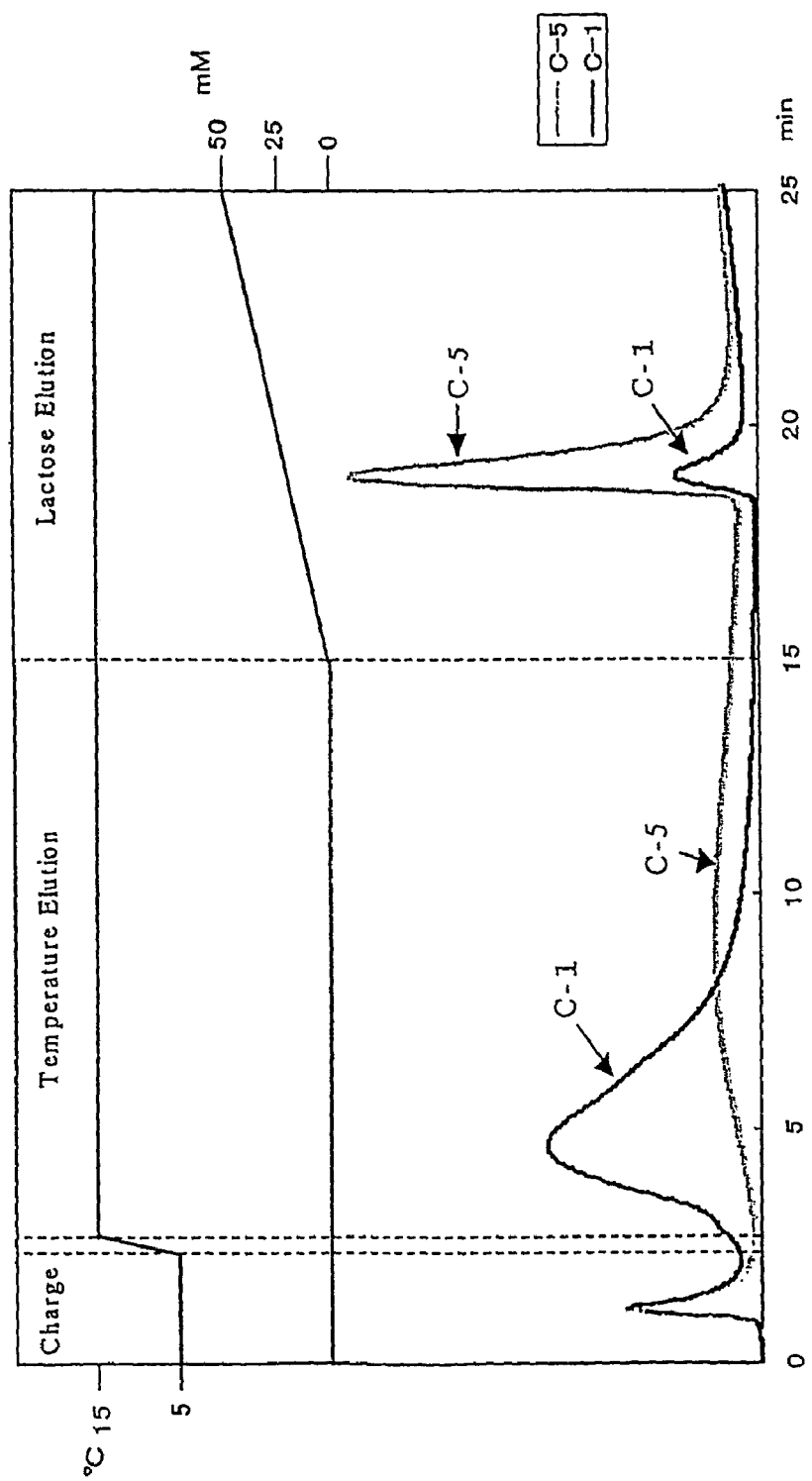
FIG. 1 shows chromatograms when the purification of human transferrin was performed by the technique of Purification Example with column (C-1) and comparison column (C-5).

In the present invention, the target substance means a biocomponent such as an antigen, a virus, a cell, a sugar chain, a sugar protein, an acceptor in the cell surface, an enzyme-substrate analog, an enzyme inhibitor, a nucleic acid and a hormone acceptor, a biologically active substance, a drug and a recombinant protein. Affinity chromatography is utilized in separating the target substance from a complicated biocomponent mixture to purify them; separating an unmodified target substance from a modified material; and taking a small amount of a target substance out of a large amount of impurities.

In the present invention, the substance A having specific affinity for the target substance A means a ligand having specific bindability to the target substance and includes, for example, an enzyme, an antibody, a lectin, a nucleic acid, a vitamin and a cell.

In the present invention, the low-molecular substance B means a compound having a molecular weight of not higher than 1,000 and includes a prosthetic group such as NAD and NADP, and a hapten sugar as the representative examples.

In the present invention, the linear or crosslinked stimulus responsive polymer having no affinity for the substance A means a polymer which causes a structural change by a physical stimulus and includes, for example, alkylamine substituted products of poly(N-acryloyl succinimide) such as poly(N-isopropyl acryl-amide), poly(N-acryloyl piperidine), poly(N-propyl acrylamide), poly(N,N-diethyl acrylamide), poly (N-cyclopropyl acrylamide), poly(N-acryloyl pyrrolidine), poly (N,N-ethylmethyl acrylamide) and poly (N-ethyl acrylamide). Further, the introduction of a crosslinked structure thereinto can be attained by adding a polyfunctional crosslinking agent such as an alkyldiamine in the substitution reaction.

The above described physical stimulus is, for example, temperature. In other words, the change in molecular recognizability of a molecule which interacts with a target substance by varying temperature can be attained, for example, by compositing a heat responsive polymer therewith. For example, chromatographic packings chemically modified with a polyalkylamide or its copolymer having an amino group, a carboxyl group, a hydroxyl group or the like at the terminal of the composite can be illustrated. The chemically modified support includes, for example, a silica support.

Depending on the concrete stimulus responsive polymer used, other stimuli such as light, magnetic field, electrical field and vibration can be applied. Stimulus responsive polymers are often called "intelligent polymers".

Stimulus responsive polymers are characterized by undergoing a structural and reversible change of their physicochemical properties when exposed to a right stimulus having a right intensity or a right level (a critical level of stimulus or a critical intensity of stimulus). This change can be a conversion of remarkable hydrophobicity to remarkable hydrophilicity or vice versa. The exact level/intensity and the type of stimulus to be required depend on the structure of the polymer and will often depend on other conditions (a solvent, solutes such as a salt and the like). The most well-known and most utilized polymers of this type respond to heat (heat responsive polymers or temperature responsive polymers). The temperature responsive polymers are recognized by having a sharp phase transition temperature or a temperature limit at which they convert from remarkable hydrophilicity to remarkable hydrophobicity or vice versa. With the temperature responsive polymer in a solution the change in conformation/physicochemical properties occurs at a so-called critical solution temperature (CST).

With the temperature responsive polymers in an aqueous solution system there is a lower critical solution temperature (LCST) or an upper critical solution temperature (UCST). The polymers having an LCST change its hydrophilic conformation to a hydrophobic conformation when temperature passes the LCST from a temperature of lower than the LCST. The polymers having an UCST show the opposite change when temperature passes the UCST from a temperature of higher than the UCST. The exact values of the LCST and UCST depend on the polymers selected and other conditions applied (solvents, solutes and the like).

As stated above, one of the characteristic features of the present invention when a temperature sensitive polymer is used is that its binding to and its release from a ligand are performed at the opposite side of the CST to be applied.

The stimulus responsive polymer preferably has smaller affinity for a target substance than the affinity between the target substance and the covalently bonded ligand. Preferably, there is no remarkable affinity between the ligand and the heat responsive polymer.

Examples of the basic constituting unit of the temperature responsive polymer include homopolymers and copolymers of an N-alkyl (meth)acrylamide such as N-isopropyl (meth) acrylamide, N-(meth)acryloyl piperidine, N-propyl (meth) acrylamide, N,N-diethyl (meth)acrylamide, N-cyclopropyl (meth)acrylamide, N-(meth)acryloyl pyrrolidine, N,N-ethylmethyl (meth)acrylamide and N-ethyl (meth)acrylamide, and copolymers thereof with monomers containing a functional group such as a carboxyl group, an amino group, a hydroxysuccinimide group, a thiol group, an imino group and an epoxy group in order to chemically composites a molecule which interacts with a target substance.

Examples of the polyalkyl acrylamide to be used in the method of the present invention include poly(N-isopropyl acrylamide)-lectin composites.

Examples of the target substance and the molecule which interacts with the target substance include biocomponents composed of amino acids, sugars, nucleic acids and the like, and organic compounds having a molecular weight of not higher than 1,000. The amount of a ligand to be chemically composited with a stimulus responsive polymer can arbitrarily be controlled and is preferably 0.1 to 50% based on the constitution of the composite. Further, the physical and chemical properties of the stimulus responsive polymer can be varied by controlling the compositing amount of the molecule which interacts with the target substance. For example, poly(N-isopropyl acrylamide) has a lower critical solution temperature of around 32° C. if it is a homopolymer, and can be controlled by the compositing amount of the molecule which interacts with the target substance.

Separation Material (For Example, Chromatographic Packing).

The separation material to be used in the present invention method comprises a base matrix (carrier) which can be based on an organic and/or inorganic material. When the liquid to be used is aqueous, the base matrix is preferably hydrophilic. This particularly applies to target substances which are biomolecules of the above described type.

The base matrix is preferably based on a polymer which preferably is water insoluble and more or less water swellable. Hydrophobic polymers which have been modified to be hydrophilic are included in this definition. Suitable polymers include polyhydroxy polymers (for example, polyhydroxy polymers based on polysaccharides such as agarose, dextran, cellulose, starch and pullulan and synthetic polymers (for example, polyacrylamide, polymethacrylamide, poly(hydroxyalkylvinyl ethers), poly (hydroxyalkyl acrylates) and polymethacrylates (for example, polyglycidyl methacrylate), polyvinyl alcohols and polymers based on styrene and divinylbenzene, and copolymers in which two or more monomers corresponding to the above described polymers are included. Water soluble polymers can be modified to be insoluble, for example, by crosslinking or by bonding them to water soluble to an insoluble substance by adsorption or covalent binding. Hydrophilic groups can be introduced on hydrophobic polymers (for example, on copolymers of monovinyl- or divinylbenzene) by polymerization of a monomer having a group convertible to a hydroxyl group or by hydrophilization of the final polymer (for example, by adsorption of a suitable compound such as a hydrophilic polymer).

Suitable inorganic materials to be used in a base matrix are silica, zirconium oxide, graphite, tantalum oxide and the like.

A preferred matrix is the one that is lacking in a group unstable against hydrolysis such as a silane group, an ester group, an amide group and a group present in silica in the form of such a group.

The base matrix can be either porous or non-porous. This means that the base matrix can be fully or partially permeable (porous) or completely impermeable (non-porous) to the compound to be removed.

The pore can have a size of not smaller than 0.1 $\mu$m (for example, not smaller than 0.5 $\mu$m) and this means that a sphere having a diameter of not smaller than 0.1 $\mu$m (for example, a sphere having a diameter of not smaller than 0.5 $\mu$m) can pass through the pore. The liquid to be applied can flow through this type of the pore system (through-pore system). When the support matrix is in the form of beads packed into a separation material, the ratio of the pore diameter of the through-pore system to the diameter of the particles is typically 0.01–0.03, preferably 0.05–0.2. Pores having a size of not smaller than 0.1 $\mu$m (for example, not smaller than 0.5 $\mu$m) are often called macropores.

The base matrix can have pores having a size of not greater than 0.5 $\mu$m (for example, not greater than 0.1 $\mu$m) and this means that only spheres having a diameter of not greater than 0.5 $\mu$m (for example, not greater than 0.1 $\mu$m) can pass through the pores. Pores having a size of not greater than 0.5 $\mu$m (for example, not greater than 0.1 $\mu$m) are often called micropores.

In a particularly interesting embodiment of the present invention, the base matrix is in the form of irregular particles or spherical particles having a size of 1 to 1000 $\mu$m, preferably 5 to 50 $\mu$m for high performance applications and 50 to 300 $\mu$m for preliminary (preparative) purposes.

Further, the base matrix can be in form of a monolith having at least macropores as defined above. Alternative geometric form is the interior walls of tubes and the like.

The stimulus responsive polymer as defined above can be bonded to the base matrix in its outer surfaces and/or in its interior surfaces (macropore surfaces and/or micropore surfaces). The stimulus responsive polymer can also be part of the polymer constituting the base matrix as such. The stimulus responsive polymer can be bonded to the base matrix by physical adsorption and/or covalent bonding, preferably the latter.

Ligand

A ligand can be bonded to the stimulus responsive polymer either before or after the polymer has been bonded to the base matrix or incorporated into the base matrix. The binding to the stimulus responsive polymer can be done by affinity bonds or covalent bonds, preferably the latter. One typical type of the ligand binds to the target substance by more or less a pure ionic (electrostatic) interaction. Alternatively, the binding includes more complicated interactions such as affinity binding (affinity adsorption). As to the ionic interaction, the ligand comprises a positively or negatively charged substance (ion exchange; the immobilized substance being selected from a primary amine, a secondary amine, a tertiary amine and a quaternary ammonium, a sulfonate salt, a phosphonate salt, a phosphate salt, a group such as a carboxyl group and the like). More complicated interactions are illustrated by the ligand of the affinity members in pairs:

(a) antibodies and antigens/haptens.
(b) lectins and carbohydrate structures.
(c) IgG binding proteins and IgG.
(d) polymeric chelators and chelates.
(e) complementary nucleic acids.

Further, the affinity members include substances which participate in catalytic reactions (for example, enzymes, enzyme substrate, auxiliary enzymes, cosubstrates and the like). Members of cell-cell interactions and cell-cell surface interactions and synthetic substances of in vivo-produced affinity members are also included. The term "ligand" also includes more or less complicated organic molecules (for example, lectins) which are bonded through affinity to complicated biomolecules such as those having oligopeptide or polypeptide structures (including proteins), oligonucle-otide and polynucle-otide structures (including nucleic acids), oligosaccharide or polysaccharide structures and the like.

The polymeric compound of the present invention can be prepared as follows. One or more monomers of the starting materials of the polymeric compound and a polymerization initiator are dissolved in a polymerization solvent and the polymerization is initiated by heating or the like. At this time, to obtain a gel structure containing such a polymeric compound, a bifunctional monomer can be dissolved in the polymerization solvent. Furthermore, to modify the molecular weight of the polymeric compound or to introduce a reactive functional group to the terminal of the polymeric compound at this time, a chain transfer agent can be dissolved in the polymerization solvent. After the polymerization reaction, the product can be reprecipitated in a solvent which does nor dissolve the product to obtain a target temperature stimulus responsive polymeric compound.

The polymeric compound of the present invention can be immobilized in the surface of a carrier such as silica and a polymer gel, for example, with the use of the reactive functional group introduced into its terminal. Also, the polymeric compound can be immobilized in the surface of a carrier such as silica and a polymer gel by immobilizing a polymerization initiator in the surface of a solid such as silica gel and a polymer gel and subsequently dissolving one or more monomers of the starting materials of the polymeric compound in a polymerization solvent to initiate polymerization reaction by heating and the like in the presence of the carrier such as silica and a polymer gel on which the polymerization initiator has been immobilized. In this instance, to obtain a gel structure of the polymeric compound a bifunctional crosslinking agent can further be dissolved in the polymerization solvent. In addition, to modify the molecular weight of the polymeric compound or to introduce a reactive functional group thereinto in this instance, a chain transfer agent can be dissolved in the polymerization solvent. Materials containing this polymeric compound can be applied to various liquid chromatographic carriers, adsorption/purification materials such as adsorbents, releasing agents such as bioproducts and intelligent polymers.

The methods of immobilizing the substance A having specific affinity for a target substance, the low-molecular substance B having specific affinity for the substance A and the stimulus responsive polymer include, for example, a method of introducing the substance A and the substance B into the stimulus responsive polymer by the copolymerization with the stimulus responsive polymer or by the reaction with a functional group on the stimulus responsive polymer chain and subsequently immobilizing the resulting polymer on a separation material; a method of independently immobilizing the substance A-introduced stimulus responsive polymer and the substance B-introduced stimulus responsive polymer in the surface of a separation material; a method of immobilizing the substance A alone in the surface of a separation material and subsequently introducing the substance B-introduced stimulus responsive thereinto with the use of the functional groups remaining in the surface of the separation material; and a method of reversely immobilizing the substance B alone in the surface of a separation material and subsequently introducing the substance A-introduced stimulus responsive polymer thereinto with the use of the functional groups remaining in the surface of the separation material. It is preferred that at the time of the immobilization reaction the compound having the substance A and the compound having the substance B are previously mixed and then immobilized in the surface of a separation material in such a state that the substance A and the substance B can be close to each other.

The immobilization reaction most efficiently proceeds at a pH ranging from 8 to 10. When a protein such as a lectin is to be bonded, a sodium bicarbonate buffer (0.2 to 0.25 M) containing 0.5M NaCl and having a pH of 8.5 to 9 is suitable.

As one preferred embodiment of the separation material of the present invention, the target substance is a sugar chain or a sugar protein, and the substance A having specific affinity for the target substance is a sugar affinity substance such as lectins including, for example, RCA 120, *Conavalia ensiformis* (concan-valin A), *Lens culinaris* (lentil) lectin, *Triticum vulgaris* (wheat malt) lectin, *Arachis hypogaea* (peanut) lectin and *Richinus communes* lectin. In this instance, the low-molecular substance B having specific affinity for the substance A includes a hapten sugar, and the stimulus responsive polymer includes poly(N-isopropyl acrylamide).

When a temperature responsive polymer prepared by substituting the succinimide group of poly(N-acryloyl succinimide) with an amine compound is used as the stimulus responsive polymer, a separation material can be obtained by rendering the poly(N-acryloyl succinimide) water soluble by introducing a compound having an amino group in an amount of 50 to 97 mol %, preferably 70 to 95 mol %, more preferably 80 to 90 mol %, based on the succinimide group of the poly(N-acryloyl succinimide), into the poly(N-acryloyl succinimide), then introducing the substance A into the resulting water soluble polymer chain in the presence of the low molecular substance B and subsequently immobilizing the resulting polymer on a separation material or immobilizing the water soluble polymer on the separation material in the presence of both of the substance A and the low-molecular substance B.

Separation/purification of a substance can be conducted by adsorbing a target substance on a separation material supporting one of the stimulus responsive polymers (1) to (4) in the above described Paragraph [0008] and varying the molecular structure of the stimulus responsive polymer while changing or not changing the solution composition of an eluent such as the salt concentration and the pH to effect the competitive reaction between the target substance and the low-molecular substance B, thereby eluting the target substance.

When the stimulus responsive polymers (1) to (5) in the above described Paragraph [0008] are temperature responsive polymers, separation/purification of a substance can be conducted by adsorbing a target substance on a separation material supporting one of the stimulus responsive polymer at a temperature of not higher than the lower critical solution temperature (LCST) if the stimulus responsive polymer has a lower critical solution temperature (LCST) or at a temperature of not lower than the upper critical solution temperature (UCST) if the stimulus responsive polymer has an upper critical solution temperature (UCST) and subsequently varying the molecular structure of the stimulus responsive polymer by changing the column temperature to exceed the critical solution temperature while changing or not changing the liquid composition such as the salt concentration of an eluent and the pH to effect the competitive reaction between the target substance and the low-molecular compound B, thereby eluting the target substance.

EXAMPLES

The present invention will now be explained in more detail by the following examples which, however, are in no way intended to restrict the invention.

Separation Material Preparation Examples

Separation materials preparation examples were given below when *Ricinus communis* lectin (RCA 120) was used as the lectin; lactose was used as the hapten sugar for the RCA 120; and Sepharose was used as the separation material.

The lactose was reacted in an ammonium bicarbonate saturated aqueous solution for 48 hours and converted into β-lactosylamine.

After dissolving N-(acryloyloxy) succinimide (6.30 g, 37.2 mmol) and AIBN (50 mg) in benzene (450 ml), polymerization reaction was carried out at 60° C. for 24 hours. After completion of the polymerization, reprecipitation from tetrahydrofuran (THF) was performed to obtain poly(N-acryloyl succinimide) as a white polymer (6.12 g, 98%).

EAH Sepharose 4B (Amersham Pharmacia Biotech) was used as the separation material.

Further, an NHS-activated Hi-Trap Column (1 ml) (Amersham Pharmacia Biotech) was used as the prepacked column.

Preparation Example 1

After dissolving poly(N-acryloyl succinimide) (1.0 g), isopropylamine (314.8 mg) and β-lactosylamine (10.1 mg) in 3 ml of dimethylformamide (DMF), the mixture was stirred at room temperature for 36 hours to effect reaction. After completion of the reaction, the polymer was subjected to reprecipitation to obtain a white water soluble polymer (0.81 g). This water soluble polymer was reacted with RCA 120 in PBS buffer (pH 7.2) in the presence of lactose. (10 mg) at 4° C. for 12 hours, and then the reaction solution was introduced into a column (1 ml) packed with EAH Sepharose 4B to effect immobilization reaction at 4° C. for 6 hours. After completion of the immobilization reaction, 1 ml of PBS buffer solution containing ethylenediamine (0.01 mg) was introduced thereinto and after the column thus prepared was left to stand at 4° C. for 12 hours, the remaining succinimide groups were inactivated with an ethanolamine solution [prepared by dissolving ethanolamine (3.05 g) and NaCl (2.92 g) in 100 ml of distill d water] to prepare a column (C-1).

Preparation Example 2

After dissolving poly(N-acryloyl succinimide) (1.0 g), isopropylamine (314.8 mg) and β-lactosylamine (50.5 mg) in 3 ml of dimethylformamide (DMF), the mixture was stirred at room temperature for 36 hours to effect reaction. After completion of the reaction, the polymer was subjected to reprecipitation to obtain a white water soluble polymer (0.81 g). The water soluble polymer was then reacted with RCA 120 (5 mg) in PBS buffer (pH 7.2) in the presence of lactose (10 mg) at 4° C. for 12 hours, and then the reaction solution was introduced into a column (1 ml) packed with EAH Sepharose 4B to effect immobilization reaction at 4° C. for 6 hours. After completion of the immobilization reaction, 1 ml of PBS buffer solution containing ethylenediamine (0.01 mg) was introduced therein and after allowing the column thus prepared was left to stand at 4° C. for 12 hours, the remaining succinimide groups were inactivated with an ethanolamine solution to prepare a column (C-2).

Preparation Example 3

After dissolving poly(N-acryloyl succinimide) (1.0 g), isopropylamine (314.8 mg) and β-lactosylamine (10.1 mg) in 3 ml of dimethylformamide (DMF), the mixture was stirred at room temperature for 36 hours to effect reaction. After completion of the reaction, the polymer was subjected to reprecipitation to obtain a white water soluble polymer (0.81 g). The water soluble polymer was then reacted with RCA 120 (5 mg) in PBS buffer (pH 7.2) in the presence of lactose (10 mg) at 4° C. for 12 hours, and then the reaction solution was introduced into a column (1 ml) packed with an NHS-activated Sepharose carrier which had been treated with ethylenediamine solution to introduce amino groups thereinto to effect the immobilization reaction at 4° C. for 6 hours. After completion of the immobilization reaction, 1 ml of PBS buffer solution containing ethylenediamine (0.01 mg) was introduced therein and after the column thus prepared was left to stand at 4° C. for 12 hours, the remaining succinimide groups were inactivated with an ethanolamine solution [prepared by dissolving ethanolamine (3.05 g) and NaCl (2.92 g) in 100 ml of distilled water] to prepare a column (C-3).

Comparative Preparation Example 1

Preparation Without Introducing Lactose into Stimulus Response Polymer

After dissolving poly(N-acryloyl succinimide) (1.0 g) and isopropylamine (314.8 mg) in 3 ml of dimethylformamide (DMF), the mixture was stirred at room temperature for 36 hours to effect reaction. After completion of the reaction, the polymer was subjected to reprecipitation to obtain a white water soluble polymer (0.81 g). The water soluble polymer was then reacted with RCA120 (5 mg) in PBS buffer (pH 7.2) in the presence of lactose (10 mg) at 4° C. for 12 hours, and then the reaction solution was introduced into a column (1 ml) packed with an NHS-activated Sepharose carrier which had been treated with ethylenediamine solution to introduce amino groups thereinto to effect immobilization reaction at 4° C. for 6 hours. After completion of the immobilization reaction, 1 ml of PBS buffer solution containing ethylenediamine (0.01 mg) was introduced thereinto and after the column thus prepared was left to stand at 4° C. for 12 hours, the remaining succinimide groups were inactivated with an ethanol-amine solution [prepared by dissolving ethanolamine (3.05 g) and NaCl (2.92 g) in 100 ml of distilled water] to prepare a column (C-4).

Comparative Preparation Example

Preparation Example Without Introducing Stimulus Response Polymer

A PBS buffer solution (pH 7.2) containing RCA 120 (5 mg) was introduced into a column (1 ml) packed with an NHS-activated Sepharose carrier in the presence of lactose (10 ml) to reaction was conducted at 4° C. for 4 hours. After completion of the immobilization reaction, the remaining succinimide groups were inactivated with an ethanolamine solution [prepared by dissolving ethanolamine (3.05 g) and NaCl (2.92 g) in 100 ml of distilled water] to prepare a column (C-5).

Separation/Purification Examples

As the example of separation and purification, temperature control of adsorption and desorption of asialotransferrin was performed with the use of a glycoprotein (human transferrin). This effected the separation of asialotransferrin from transferrin with sialic acid. The columns prepared by the methods described in the Preparation Examples and Comparative Examples were connected to an HPLC apparatus (LC-6A, Shimadzu). The other conditions were as follows.

Flow rate: 1.0 ml/min; Detection: UV (280 nm); Eluent: 0.01 M PBS buffer (pH 7.4)

A 25 nmol of human transferrin (Sigma Chemical Co., Ltd.) was treated with 0.1 mU of sialidase (from *Arthrobacter ureafaciens*, Sigma Chemical Co., Ltd.) in 1 ml of 50 mM oxalic acid buffer (pH 5.0) at 37° C. for 6 hours to prepare a sample.

Purification Example 1

After mounting a column (C-1) onto the HPLC apparatus, solution flow was initiated, and after equilibration in a thermostat set at 5° C., the sample (50 µl) was injected to adsorb asialotransferrin on the column. After eluting a sialic acid adduct not retained on the column (4 to 5 minutes), the column temperature was brought to 15° C. to perform elution of the adsorbed asialotransferrin by temperature change alone. When no further eluate by temperature change (15 minutes) was found, a linear gradient of 0 to 50 mM lactose PBS buffer solution was applied (10 minutes) to perform elution of the remaining asialotrans-ferrin which had not been eluted by temperature change alone.

The chromatograms for purification of human transferrin by the method of the Purification Example 1 with the use of the column (C-1) and the comparison column (C-5) were shown in FIG. 1. As would be understood from FIG. 1, about 90% of the total adsorption amount were recovered by the elution by temperature change alone in column (C-1) while with the comparison column the recovery was not greater than 20%. The recovery by temperature elution at 15° C. with each column was summarized in Table 1.

Figure 2:
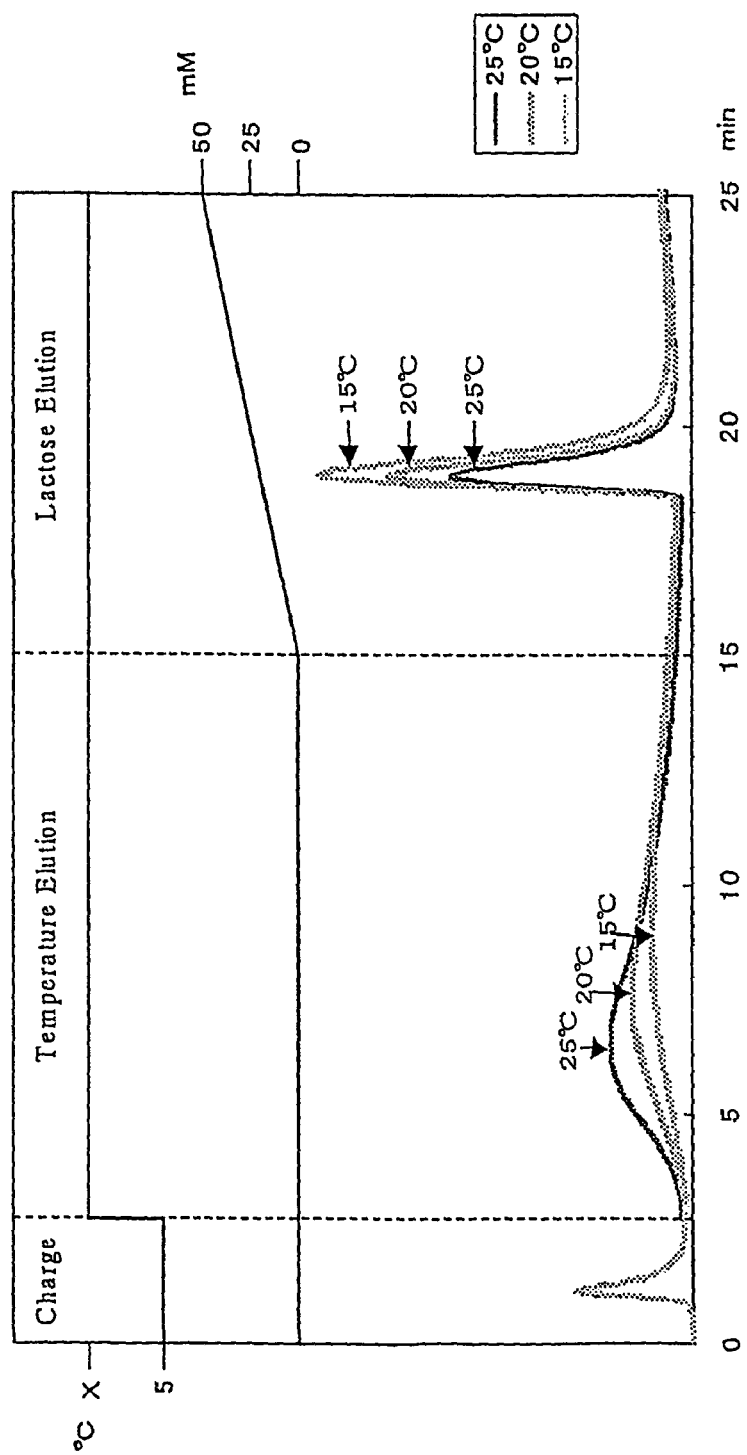
FIG. 2 shows chromatograms of comparison column (C-5) when the elution temperatures were raised from 15° C. to 20° C. and 25° C., respectively.
Figure 3:
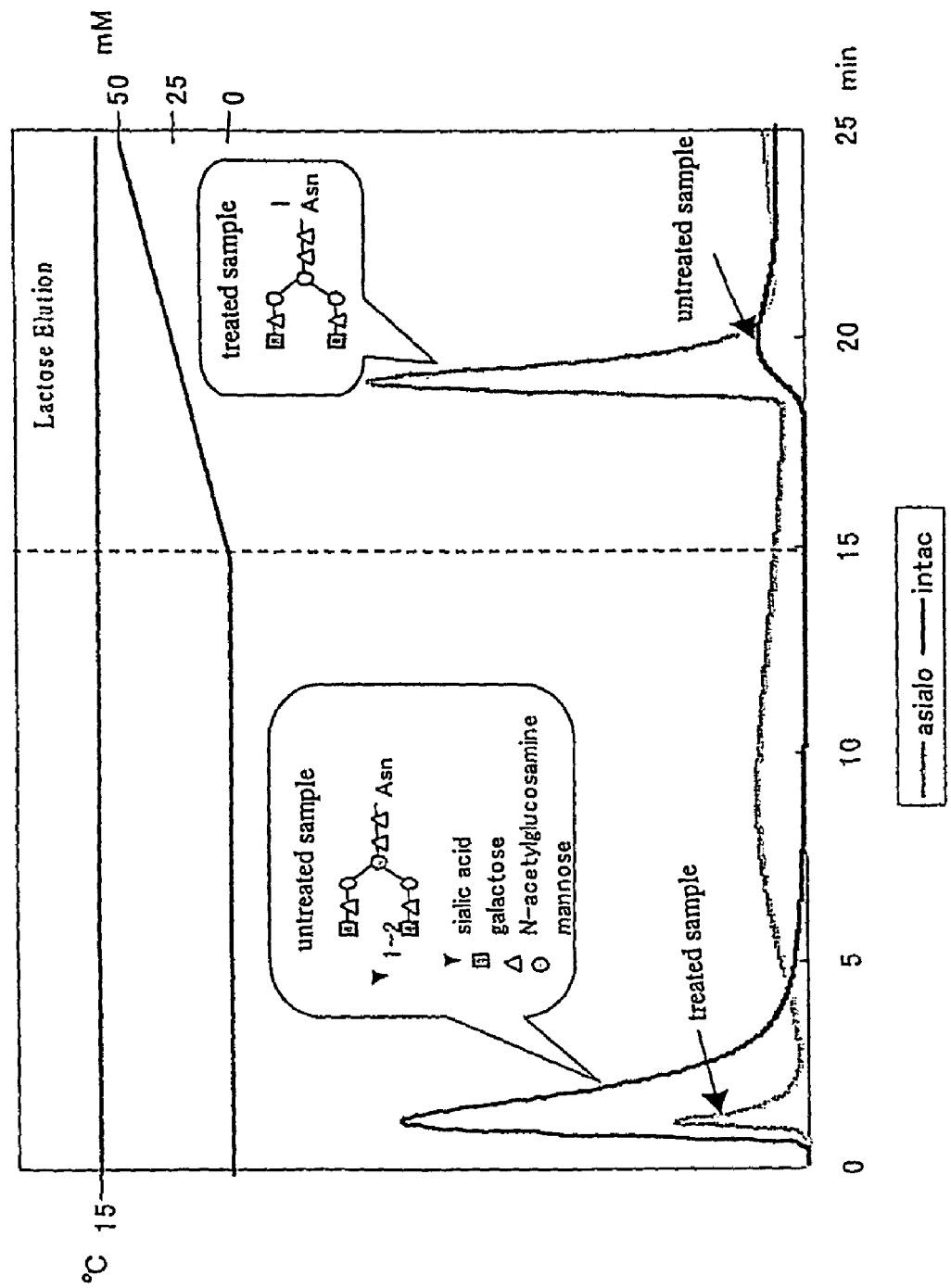
FIG. 3 shows chromatograms with the C-5 column for the sialidase-treated transfferin and the untreated human transferrin.

Further, the chromatograms of the comparison column (C-5) when the elution temperatures were raised from 15° C. to 20° C. and 25° C., respectively, were shown in FIG. 2. With the comparison column (C-5), the recovery was 50% even when the elution temperature was raised to 25° C. For reference, were shown in FIG. 3 shows the chromatograms of the C-5 column for the sialidase-treated human transferrin and the non-treated human transferrin were shown in FIG. 3. Since the sialic acid at the sugar chain terminal of the untreated human transferrin inhibited the interaction with RCA 120, the untreated human transferrin mostly passed through the column while the sample whose terminal sialic acid had been eliminated by the sialidase treatment was mostly trapped with RCA and lastly eluted by the application of the gradient of lactose.

TABLE 1

Comparison of Recovery by Change of Temperature Alone

| Column | Recovery (%) |
|---|---|
| C-1 | 92.7 |
| C-2 | 90.5 |
| C-3 | 73.1 |
| C-4 | 25.1 |
| C-5 | 26.8 |

INDUSTRIAL APPLICABILITY

The separation material of the present invention ceases to need the desalting and hapten sugar-eliminating operations and accordingly, has the following excellent effects.

(1) Affinity Chromatography of Low-Molecular Compound

It becomes possible to perform the purification by a lectin affinity chromatography for low-molecular compounds such as sugar chains in which desalting and hapten sugar-elimination are impossible or difficult.

(2) Bioassay

A bioassay to be carried out at low salt concentrations or under physiological conditions becomes easy.

(3) Increase in Detection Sensitivity

It is known that according to MADLI TOF-MS, the salt in a sample deteriorates S/N and thus, it is necessary to perform the desalting operation before measurement, particularly with traces of a sample, but with the use of the elution by temperature according to the present invention the TOF-MS measurement can be conducted without the desalting operation. Further, when affinity chromatography is performed in the pretreatment of a sample for 2D-PAGE, the sample as such can be used and a reduction in sample loss and an improvement in detection sensitivity can be expected.

Also, the separation material of the present invention enables the regeneration of carriers by temperature alone and dispenses with washing under strongly alkaline conditions which is conventionally employed and thus, the productivity can be expected.

The invention claimed is:

1. A separation material comprising a linear or crosslinked stimulus responsive polymer to which a substance A having specific affinity for a target substance and a low-molecular substance B having specific affinity for the substance A have been bonded, wherein the target substance is a sugar chain or glycoprotein; the substance A with specific affinity for the target substance is a sugar affinity substance having affinity for the specific structure of a sugar chain; the low-molecular substance B with specific affinity for the substance A is a hapten sugar; and the stimulus responsive polymer is poly (N-isopropyl acrylamide).

2. The separation material of claim 1 which is prepared by rendering a poly(N-acryloyl succinimide) compound water soluble by introducing a compound having an amino group in an amount of 50–97 mol %, based on the succinimide group of the poly(N-acryloylsuccinimide), into the succinimide groups of the poly(N-acryloylsuccinimide), then introducing the substance A into the resulting water soluble compound in the presence of the low molecular substance B and subsequently immobilizing the resulting polymer on the separation material or immobilizing the water soluble polymer on the separation material in the presence of the substance A and the low-molecular substance B.

3. A packing for affinity chromatography comprising a separation material of claim 1.

4. A substance separation/purification method comprising adsorbing a target substance onto the separation material of claim 1 and varying the molecular structure of the stimulus responsive polymer while flowing a solution through said material and changing the solution composition and the pH to effect the competitive reaction between the target substance and the low-molecular substance B, thereby eluting the target substance.

5. A substance separation/purification method characterized by adsorbing a target substance on the separation material of claim 1 which is a temperature responsive polymer at a temperature not higher than the low critical solution temperature (LCST) if the stimulus responsive polymer has an LCST or at a temperature of not lower than the upper critical solution temperature (UCST) if the stimulus responsive polymer has a UCST and varying the molecular structure of the stimulus responsive polymer by changing the column temperature to exceed the critical solution temperature while flowing a solution through said material and changing the solution composition and the pH to effect the competitive reaction between the target substance and the low-molecular substance B, thereby eluting the target substance.

6. A separation material comprising a linear or crosslinked stimulus responsive polymer to which only a substance A having specific affinity for a target substance has been bonded and a linear or crosslinked stimulus responsive polymer to which only a low-molecular substance B having specific affinity for the substance A has been bonded, wherein the target substance is a sugar chain or glycoprotein; the substance A with specific affinity for the target substance is a sugar affinity substance having affinity for the specific structure of a sugar chain; the low-molecular substance B with specific affinity for the substance A is a hapten sugar; and the stimulus responsive polymer is poly(N-isopropyl acrylamide).

7. The separation material of claim 6 which is prepared by rendering a poly(N-acryloyl succinimide) compound water soluble by introducing a compound having an amino group in an amount of 50–97 mol %, based on the succinimide group of the poly(N-acryloylsuccinimide), into the succinimide groups of the poly(N-acryloylsuccinimide), then introducing the substance A into the resulting water soluble compound in the presence of the low molecular substance B and subsequently immobilizing the resulting polymer on the separation material or immobilizing the water soluble polymer on the separation material in the presence of the substance A and the low-molecular substance B.

8. A packing for affinity chromatography comprising a separation material of claim 6.

9. A substance separation/purification method comprising adsorbing a target substance onto the separation material of claim 6 and varying the molecular structure of the stimulus responsive polymer while flowing a solution through said material and changing the solution composition and the pH to effect the competitive reaction between the target substance and the low-molecular substance B, thereby eluting the target substance.

10. A substance separation/purification method characterized by adsorbing a target substance on the separation material of claim 6 which is a temperature responsive polymer at a temperature not higher than the low critical solution temperature (LCST) if the stimulus responsive polymer has an LCST or at a temperature of not lower than the upper critical solution temperature (UCST) if the stimulus responsive polymer has a UCST and varying the molecular structure of the stimulus responsive polymer by changing the column temperature to exceed the critical solution temperature while flowing a solution through said material and changing the solution composition and the pH to effect the competitive reaction between the target substance and the low-molecular substance B, thereby eluting the target substance.

11. A separation material comprising a substance A having specific affinity for a target substance or a low-molecular substance B having specific affinity for substance A on a base matrix and, at the same time, supporting a linear or crosslinked stimulus responsive polymer to which the substance A or the substance B has been bonded in the surface of the separation material, wherein the target substance is a sugar chain or glycoprotein; the substance A with specific affinity for the target substance is a sugar affinity substance having affinity for the specific structure of a sugar chain; the low-molecular substance B with specific affinity for the substance A is a hapten sugar; and the stimulus responsive polymer is poly(N-isopropyl acrylamide).

12. The separation material of claim 11 which is prepared by rendering a poly(N-acryloyl succinimide) compound water soluble by introducing a compound having an amino group in an amount of 50–97 mol %, based on the succinimide group of the poly(N-acryloylsuccinimide), into the succinimide groups of the poly(N-acryloylsuccinimide), then introducing the substance A into the resulting water soluble compound in the presence of the low molecular substance B and subsequently immobilizing the resulting polymer on the separation material or immobilizing the water soluble polymer on the separation material in the presence of the substance A and the low-molecular substance B.

13. A packing for affinity chromatography comprising a separation material of claim 11.

14. A substance separation/purification method comprising adsorbing a target substance onto the separation material of claim 11 and varying the molecular structure of the stimulus responsive polymer while flowing a solution through said material and changing the solution composition and the pH to effect the competitive reaction between the target substance and the low-molecular substance B, thereby eluting the target substance.

15. A substance separation/purification method characterized by adsorbing a target substance on the separation material of claim 11 which is a temperature responsive polymer at a temperature not higher than the low critical solution temperature (LCST) if the stimulus responsive polymer has an LCST or at a temperature of not lower than the upper critical solution temperature (UCST) if the stimulus responsive polymer has a UCST and varying the molecular structure of the stimulus responsive polymer by changing the column temperature to exceed the critical solution temperature while flowing a solution through said material and changing the solution composition and the pH to effect the competitive reaction between the target substance and the low-molecular substance B, thereby eluting the target substance.

* * * * *